(12) United States Patent
Akiyama et al.

(10) Patent No.: US 9,497,552 B2
(45) Date of Patent: Nov. 15, 2016

(54) CAPACITIVE TRANSDUCER, CAPACITIVE TRANSDUCER MANUFACTURING METHOD, AND OBJECT INFORMATION ACQUISITION APPARATUS

(71) Applicant: CANON KABUSHIKI KAISHA, Tokyo (JP)

(72) Inventors: Takahiro Akiyama, Kawasaki (JP); Kazutoshi Torashima, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/922,100

(22) Filed: Jun. 19, 2013

(65) Prior Publication Data

US 2014/0010388 A1 Jan. 9, 2014

(30) Foreign Application Priority Data

Jul. 6, 2012 (JP) .................................. 2012-151939

(51) Int. Cl.
- *H04R 19/01* (2006.01)
- *B06B 1/02* (2006.01)
- *G01H 11/06* (2006.01)

(Continued)

(52) U.S. Cl.
CPC ........... *H04R 19/013* (2013.01); *B06B 1/0292* (2013.01); *G01H 11/06* (2013.01); *G01N 29/2406* (2013.01); *G01N 29/348* (2013.01)

(58) Field of Classification Search
CPC .... H04R 19/00; H04R 19/005; H04R 19/01; H04R 19/013; H04R 19/02; G01H 11/00; G01H 11/06
USPC .......................... 381/191, 113, 116, 190, 174
See application file for complete search history.

(56) References Cited

U.S. PATENT DOCUMENTS

| | | | |
|---|---|---|---|
| 5,870,351 A | 2/1999 | Ladabaum et al. | |
| 7,477,572 B2 * | 1/2009 | Caronti et al. | ............... 367/140 |
| 2001/0043028 A1 | 11/2001 | Ladabaum | |

(Continued)

FOREIGN PATENT DOCUMENTS

| | | |
|---|---|---|
| CN | 101712028 A | 5/2010 |
| CN | 102076428 A | 5/2011 |

(Continued)

OTHER PUBLICATIONS

Caronti, Alessandro, et al., The effects of membrane metallization in capacitive microfabricated ultrasonic transducers, 2004, Acoustical Society of America, pp. 651-657.*

(Continued)

*Primary Examiner* — Ahmad F Matar
*Assistant Examiner* — Sabrina Diaz
(74) *Attorney, Agent, or Firm* — Fitzpatrick, Cella, Harper & Scinto (57) ABSTRACT

Provided is a capacitive transducer having broadband frequency characteristics. The capacitive transducer includes an element which has multiple kinds of cells, each cell including: a first electrode; a vibrating film including a second electrode, the second electrode being opposed to the first electrode with a gap; and a support portion that supports the vibrating film so as to form the gap. The multiple kinds of cells have different ratios of an area of one of the first electrode and the second electrode to an area of the gap when viewed from a normal direction of the vibrating film. The first electrodes or the second electrodes in the multiple kinds of cells are electrically connected together.

21 Claims, 4 Drawing Sheets

(51) Int. Cl.
*G01N 29/24* (2006.01)
*G01N 29/34* (2006.01)

(56) References Cited

U.S. PATENT DOCUMENTS

| | | |
|---|---|---|
| 2001/0043029 A1 | 11/2001 | Ladabaum |
| 2007/0059858 A1 | 3/2007 | Caronti et al. |
| 2007/0193354 A1 | 8/2007 | Felix et al. |
| 2008/0205668 A1* | 8/2008 | Torii et al. .......... 381/113 |
| 2010/0053618 A1* | 3/2010 | Nakajima et al. ......... 356/432 |
| 2012/0163124 A1 | 6/2012 | Akiyama et al. |
| 2012/0262770 A1 | 10/2012 | Torashima et al. |
| 2012/0266682 A1 | 10/2012 | Torashima et al. |
| 2013/0037696 A1 | 2/2013 | Iwata et al. |

FOREIGN PATENT DOCUMENTS

| | | |
|---|---|---|
| EP | 1779784 A1 | 2/2007 |
| EP | 1779784 A | 5/2007 |
| EP | 1779784 A1 | 5/2007 |

OTHER PUBLICATIONS

U.S. Appl. No. 13/983,287, filed Aug. 1, 2013 Applicant: Ayako Kato, et al.
U.S. Appl. No. 13/926,532, filed Jun. 25, 2013 Applicant: Kazutoshi Torashima, et al.
U.S. Appl. No. 13/920,909, filed Jun. 18, 2013 Applicant Kazutoshi Torashima, et al.
Caronti, Alessandro, et al., The Effects of Membrane Metallization in Capacitive Microfabricated Ultrasonic Transducers, Acoustical Society of America, pp. 651-657, Feb. 2004.
European Search Report dated Nov. 22, 2013 issued in corresponding European Patent Application No. 13174471.6.
Chinese Office Action dated Feb. 5, 2015 corresponding to Chinese Patent Application No. 201310273140.1.
Korean Office Action dated May 14, 2015 in corresponding Application No. 10-2013-0076247.

* cited by examiner

CAPACITIVE TRANSDUCER, CAPACITIVE TRANSDUCER MANUFACTURING METHOD, AND OBJECT INFORMATION ACQUISITION APPARATUS

BACKGROUND OF THE INVENTION

Field of the Invention

The present invention relates to a capacitive transducer to be used as an ultrasonic transducer or the like and a capacitive transducer manufacturing method.

Description of the Related Art

Ultrasonic transducers, which are designed to transmit and receive an ultrasonic wave, are used in a diagnosis apparatus for making a diagnosis of tumor inside a living body, for example. In recent years, a capacitive transducer using micromachining technology (capacitive micromachined ultrasonic transducer: CMUT) is being developed. The CMUT is superior to a conventional ultrasonic transducer using a piezoelectric element in obtaining broadband characteristics easily and being low in noise with a less number of vibration modes. The feature of the CMUT is to transmit or receive an acoustic wave, such as an ultrasonic wave, a sonic wave, and a photoacoustic wave (hereinafter sometimes represented by ultrasonic wave) with the use of a lightweight vibrating film. Attention is being paid on this promising technology of using the CMUT to make an accurate ultrasonic diagnosis as compared to a conventional medical diagnostic modality.

As the above-mentioned technology, a capacitive transducer that realizes broadband characteristics (characteristics with a relatively high electromechanical transformer ratio in a wide frequency domain) has been proposed, which includes a cell including a vibrating film having a high spring constant and a cell including a vibrating film having a low spring constant (see U.S. Pat. No. 5,870,351). Another capacitive transducer that realizes broadband characteristics has been proposed, which has a cell group of multiple cells having a high spring constant and a cell group of multiple cells having a low spring constant (see US 2007/0059858).

In the capacitive transducers as described above, the broadband is attained by using multiple cells including multiple vibrating films having different spring constants. Thus, the capacitive transducer typically includes multiple cells including multiple vibrating films having different areas.

The capacitive transducer is manufactured by using, for example, surface micromachining technology, mainly sacrificial layer etching technology. In the surface micromachining technology, however, a thin film portion to be shaped later into a vibrating film may adhere onto a lower surface of a gap formed by etching the sacrificial layer in a drying step following the etching of the sacrificial layer. Even when the capacitive transducer can be manufactured, the vibrating film is liable to be warped by stress, and, in particular, a vibrating film having a large area is liable to be warped because the spring constant is low. Depending on the stress distribution of the vibrating film, the vibrating film is unevenly warped to deteriorate the performance. The challenge to realize a capacitive transducer having broadband characteristics with a high electromechanical transformer ratio is to form a device by manufacturing multiple cells having different frequency characteristics of the electromechanical transformer ratios uniformly in a single element.

SUMMARY OF THE INVENTION

In view of the above-mentioned problem, according to the present invention, there is provided a capacitive transducer including an element which has multiple kinds of cells, each cell including: a first electrode; a vibrating film including a second electrode, the second electrode being opposed to the first electrode with a gap; and a vibrating film support portion that supports the vibrating film so as to form the gap. The multiple kinds of cells have different ratios of an area of one of the first electrode and the second electrode to an area of the gap when viewed from a normal direction of the vibrating film. The first electrodes or the second electrodes in the multiple kinds of cells are electrically connected together.

Further features of the present invention will become apparent from the following description of exemplary embodiments with reference to the attached drawings.

DESCRIPTION OF THE EMBODIMENTS

Figure 1A:
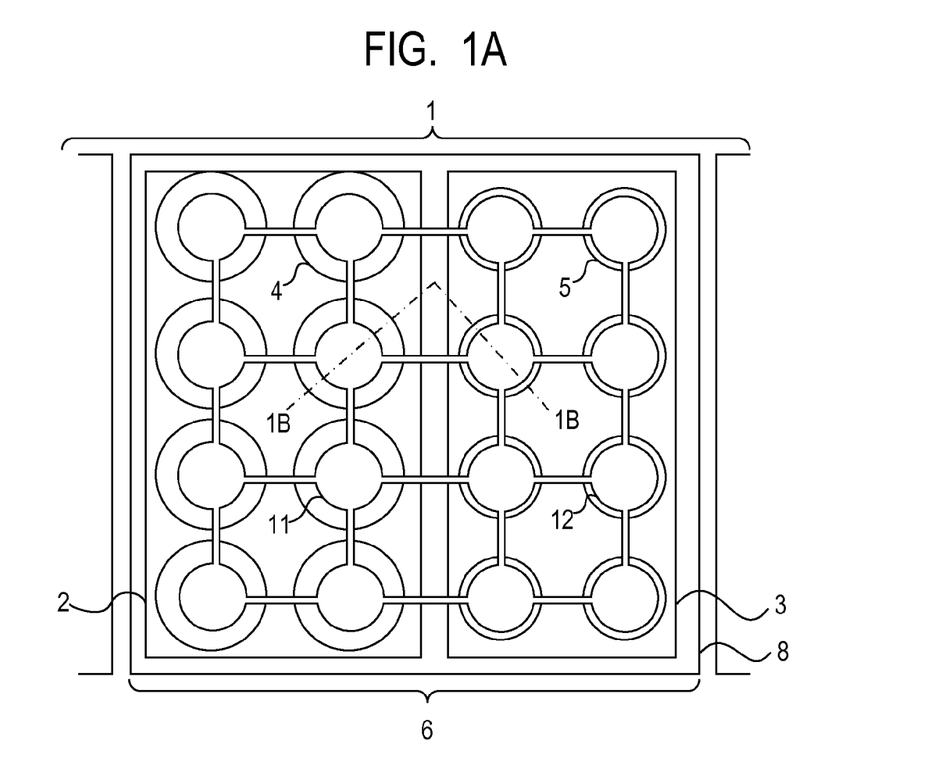
FIGS. 1A and 1B are diagrams illustrating a capacitive transducer according to an embodiment and Example 1 of the present invention.
Figure 1B:
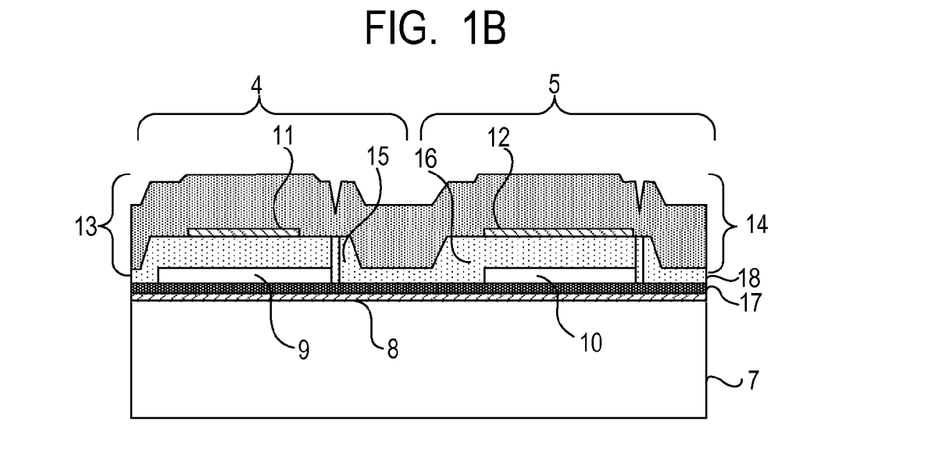
Figure 2:
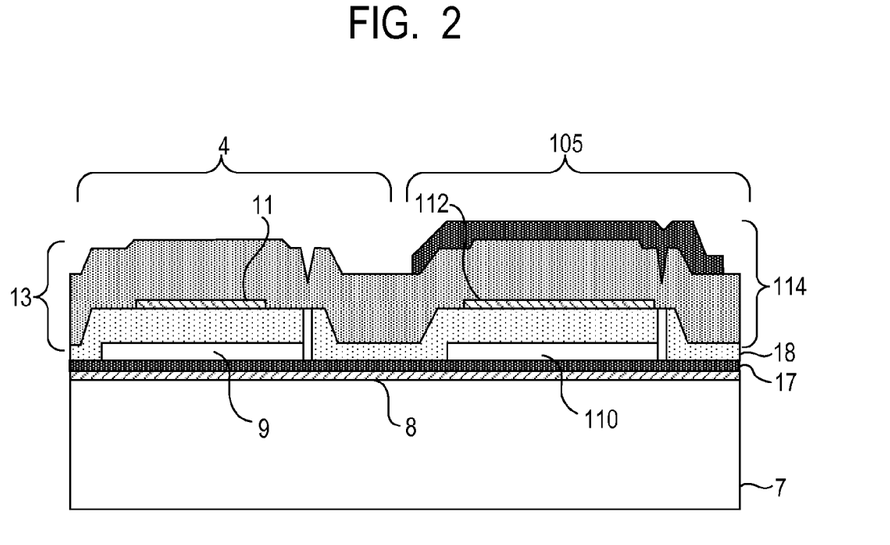
FIG. 2 is a diagram illustrating a capacitive transducer according to another embodiment and Example 2 of the present invention.

The feature of a capacitive transducer according to the present invention is to provide multiple kinds (two kinds or at least three kinds) of cells having different ratios of the area of a first electrode or a second electrode to the area of a gap when viewed from the normal direction of a vibrating film in order to realize broadband characteristics. This structural feature enables the multiple kinds of cells to be designed to have various structures. For example, the vibrating films of the multiple kinds of cells can be formed to have equal spring constants in order to facilitate the manufacturing process. Alternatively, the vibrating films of the multiple kinds of cells can be formed to have different spring constants so that the above-mentioned ratio of a cell having a large spring constant of the vibrating film may be larger than the above-mentioned ratio of a cell having a small spring constant of the vibrating film. This structural example is illustrated in FIGS. 1A and 1B, and the multiple kinds of cells can be formed to have pull-in voltages close to one another. The pull-in voltage as used herein refers to an applied voltage between the first electrode and the second electrode at which the electrostatic attractive force becomes larger than a restoring force of the vibrating film so that the vibrating film is brought into contact with a lower surface of the gap. When applied with a voltage equal to or higher than the pull-in voltage, the vibrating film is brought into contact with the lower surface of the gap. Still alternatively, the vibrating films of the multiple kinds of cells can be formed to have different areas so that the above-mentioned ratio of a cell having a small area of the vibrating film may be larger than the above-mentioned ratio of a cell having a large area of the vibrating film. Also in this structure, the pull-in voltages can be set to be close to one another. Still alternatively, the vibrating films of the multiple kinds of cells can be formed to have different thicknesses so that the above-mentioned ratio of a cell having a large thickness of the vibrating film may be larger than the above-mentioned ratio of a cell having a small thickness of the vibrating film. This structural example is illustrated in FIG. 2. Also in this structure, the multiple kinds of cells can be formed to have pull-in voltages close to one another. As described above, according to the structure of the present invention, for example, even when the vibrating films of the multiple kinds of cells have the same or close spring constants, areas, or thicknesses, a broad band of sensitivity can be realized. In those cases, the vibrating films of all the cells have close spring constants, areas, or thicknesses and can therefore be manufactured uniformly with ease. On the other hand, even when the vibrating films of the multiple kinds of cells have different spring constants, areas, or thicknesses, by appropriately varying the above-mentioned ratios among the multiple kinds of cells, for example, by causing the multiple kinds of cells to have pull-in voltages close to one another, the transmitting sensitivity or the receiving sensitivity can be improved. This can prevent the transmitting sensitivity or the receiving sensitivity from being lowered even when a common voltage applying unit is used. It should be understood that separate voltage applying units may be used for the multiple kinds of cells depending on the difference in pull-in voltage. As described above, according to the capacitive transducer of the present invention, the receiving or transmitting frequency band width can be increased, and, by appropriately designing the above-mentioned ratios, the transmitting sensitivity or the receiving sensitivity can be improved as well.

Referring to the accompanying drawings, an embodiment of the present invention is described below. FIG. 1A is a top view of a capacitive transducer 1 according to this embodiment, and FIG. 1B is a cross-sectional view taken along the line 1B-1B of FIG. 1A. The capacitive transducer 1 according to this embodiment includes two cell groups 2 and 3. The cell group 2 includes multiple cells 4, and the cell group 3 includes multiple cells 5. The cell groups 2 and 3 are electrically connected to each other, and the two cell groups form one element 6. FIG. 1A illustrates only one element 6, but the capacitive transducer 1 may include an array element including multiple elements 6. In FIG. 1A, the cells 4 and 5 are arranged in a square lattice, but may be arranged in a staggered manner or any other manner.

The cells 4 and 5 respectively include a common first electrode 8 formed on a substrate 7, gaps 9 and 10 formed by etching sacrificial layers, vibrating films 13 and 14, and support portions 15 and 16 that support the vibrating films 13 and 14. The vibrating films 13 and 14 respectively include second electrodes 11 and 12 opposed to the first electrode 8 with the gaps. In FIGS. 1A and 1B, the vibrating films 13 and 14 are circular when viewed from the normal direction of the vibrating films, but may be quadrangle, hexagonal, elliptical, or the like. The substrate 7 may be a wafer to be used for manufacturing a typical integrated circuit or a typical optical device, and may be, for example, silicon (Si), gallium arsenide (GaAs), glass (SiO2), SiC, or silicon-on-insulator (SOI). The first electrode 8 and the second electrodes 11 and 12 only need to be made of a metal thin film, as exemplified by Al, Ti, Co, Cu, Mo, and W, AlSi, AlCu, AlSiCu, TiW, TiN, and TiC as compounds thereof, and a laminate thereof. The first electrode 8 may be insulated from the substrate 7, or may be connected to the substrate 7 when the substrate 7 is made of an electrically conductive material. The substrate 7 may be integrated with the first electrode 8, and, for example, a silicon (Si) substrate itself may be used to function as the first electrode 8.

In the cells 4 and 5 of the capacitive transducer 1, the first electrodes 8 and the second electrodes 11 and 12 are electrically connected respectively to each other, and the first electrode 8 and the second electrodes 11 and 12 are insulated from each other by insulating films 17 and 18. Any one of the two insulating films 17 and 18 may be omitted. In the capacitive transducer 1, the capacitance changes with time depending on the vibrating films 13 and 14 to be vibrated. When the vibrating films 13 and 14 are periodically vibrated, an acoustic wave is generated. When receiving an acoustic wave, the vibrating films 13 and 14 are vibrated to generate an AC current.

In FIG. 1B, the vibrating films 13 and 14 are three-layer structures including the second electrodes 11 and 12, respectively. Examples of the material for the other components than the second electrodes 11 and 12 include silicon nitride, diamond, silicon carbide, silicon oxide, and polysilicon. Although not illustrated, a voltage applying unit for applying a voltage (DC voltage or AC voltage) between the first electrode 8 and the second electrodes 11 and 12 is provided.

In this embodiment for achieving the above-mentioned object of the present invention, the ratio between the area (the area when viewed from the normal direction of the vibrating film; the same applies below) of the second electrode 11 and the area of the gap 9 in the cell of the cell group 2 is different from the ratio between the area of the second electrode 12 and the area of the gap 10 in the cell of the cell group 3. It is desired that the cells inside one element 6 have uniform electromechanical transformer characteristics. This is because the electromechanical transformer ratio becomes maximum when the vibrating films operate in the same phase. According to the present invention including this embodiment, the cell group 2 and the cell group 3 are formed to have different ratios between the areas of the gaps 9 and 10 and the areas of the second electrodes 11 and above the gaps, to thereby change the frequency characteristics of the electromechanical transformer ratios and realize the broadband. In addition to this, by making an appropriate design, the electromechanical transformer characteristics of all the cells can be set to be substantially uniform to improve the electromechanical transformer ratios as well.

For example, in the case where the gaps 9 and 10 have the same area and the vibrating films 13 and 14 have the same structure, if the second electrodes 11 and 12 have different areas, negative stiffness caused by the electrostatic force occurs with different degrees when the same voltage is applied between the electrodes. Therefore, the mechanical impedances of the vibrating films 13 and 14 differ from each other when the voltage is applied. As a result, different frequency characteristics are obtained between the cell group 2 and the cell group 3, thus attaining broadband characteristics.

When the vibrating films 13 and 14 have different spring constants, the effect of obtaining broadband characteristics is enhanced more. The optimum value of the voltage to be applied to the cell depends on the spring constant of the vibrating film and the electrode area. When the cells have uniform electromechanical transformer characteristics, it is desired to set the applied voltage to be a value smaller by 10% to 20% than the voltage at which the vibrating film is brought into contact with the lower surface of the gap (pull-in voltage). This is because, although the electromechanical transformer characteristics are improved as the applied voltage becomes higher, the operation becomes unstable due to characteristics fluctuations of the cells when the applied voltage is too close to the pull-in voltage.

The "spring constant" is defined as an average displacement of a region where the first electrode and the second electrode are opposed to each other, which is caused by the electrostatic force. When the spring constant is represented by k; the capacitance, C; the average displacement of the region of the vibrating film where the electrodes are opposed to each other (hereinafter also referred to as "electrode portion"), x; and a potential difference between the first electrode and the second electrode, V, the spring constant k is expressed by the relationship of Expression 1 below.

$$k=(V^2/2)\cdot((\partial C/\partial x)/x) \quad \text{(Ex. 1)}$$

As the area of the electrode becomes smaller, a larger displacement occurs in the vibrating film due to the electrostatic force caused by a bias voltage. As the area of the electrode becomes smaller, on the other hand, the electrostatic force becomes smaller. As the area of the electrode becomes larger, a smaller displacement occurs in the vicinity of the support portion of the vibrating film. Accordingly, the relationship between the electrode area and the spring constant is a convex downward function having an extreme value. In any case, the spring constant is changed simply by changing the electrode area, and, when multiple kinds of cells having different electrode areas with respect to the gap areas are provided in one element, the band is increased. However, the electromechanical transformer ratio becomes smaller as the electrode area becomes smaller, and it is therefore desired that the electrode area be 50% or more of the area of the gap portion.

Some structures are conceivable to set different spring constants of the vibrating films 13 and 14. The thicknesses of the vibrating films 13 and 14 may be different, or the areas of the vibrating films 13 and 14 with respect to the gaps 9 and 10 may be different. Alternatively, another material may be added only onto the vibrating film 13 of one of the cells. Still alternatively, the areas of the support portions 15 and 16 may be changed to be different.

The above description is given of the area ratios of the second electrodes 11 and 12 with respect to the gap areas. However, the same effects can be obtained also in the case where the area ratios of the first electrode 8 with respect to the gaps 9 and 10 are different.

Figure 3A:
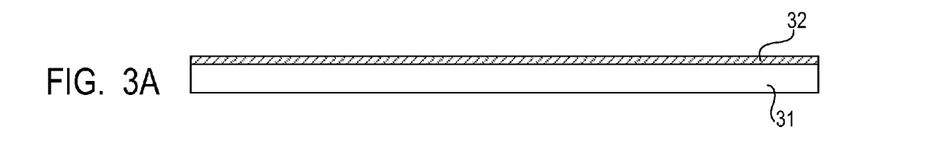
FIGS. 3A, 3B, 3C, 3D, 3E, and 3F are diagrams illustrating an exemplary method of manufacturing the capacitive transducer according to the present invention.

Referring to FIGS. 3A to 3F, an exemplary method of manufacturing the capacitive transducer according to the present invention is described below. A first electrode 32 is formed on a substrate 31 by conductor film formation, photolithography, and patterning (FIG. 3A). In this case, the first electrode 32 and the substrate 31 may be electrically connected to or insulated from each other. In the case of insulating the substrate 31 from the first electrode 32, an insulating film is formed before the first electrode 32 is formed. The gaps 9 and 10 and the membranes formed thereon illustrated in FIG. 1B are required to be smooth with less thickness fluctuations, and hence the substrate 31, the first electrode 32, and the like are required to be smooth. The gaps 9 and 10 each have a height of approximately 100 to 300 nanometers, and hence the smoothness is preferred to be approximately 1 to 2 nanometers.

Figure 3B:
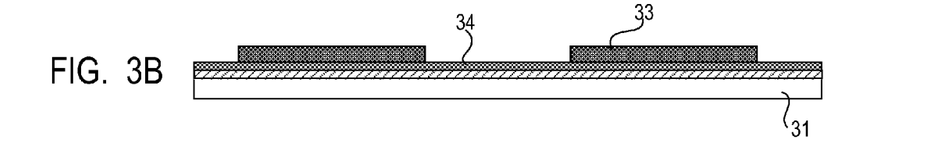

An insulating film 34 is formed. The insulating film 34 is, for example, a silicon oxide film formed by plasma-enhanced chemical vapor deposition (PECVD) and having a thickness of 50 to 150 nanometers. The insulating film 34 is not always required to be formed. Next, a sacrificial layer 33 is formed on the first electrode 32 by film formation, photolithography, and patterning (FIG. 3B). The sacrificial layer and the insulating film are also required to have high smoothness similarly to the above. In consideration of the fact that the sacrificial layer determines a cavity shape, the sacrificial layer 33 needs to be made of a material having good process selectivity with respect to surrounding materials and having less patterning fluctuations. The thickness of the sacrificial layer 33 determines the heights of the gaps 9 and 10 of FIG. 1B. The sacrificial layer 33 is therefore required to have a small thickness distribution and be smooth as described above. Examples of the material for the sacrificial layer include chromium, molybdenum, aluminum, a compound thereof, amorphous silicon, and oxide silicon.

Figure 3C:
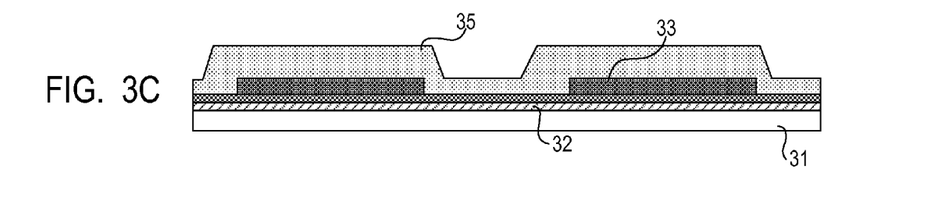
Figure 3D:
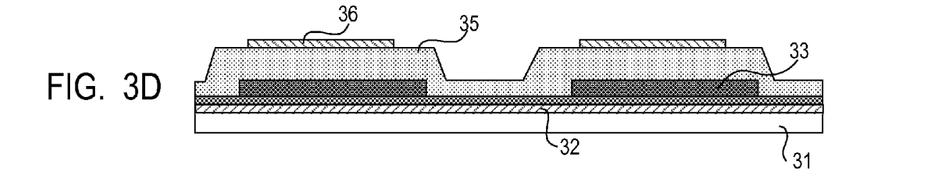

A first membrane 35 is formed on the sacrificial layer 33 (FIG. 3C). Subsequently, a conductor is formed by film formation and subjected to photolithography and patterning, to thereby form a second electrode 36 (FIG. 3D).

Figure 3E:
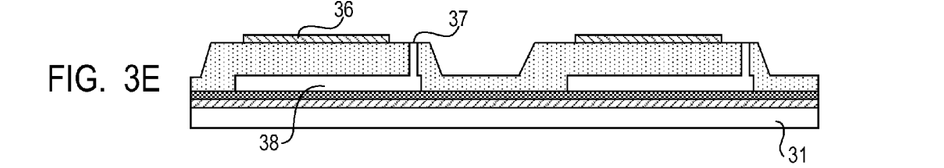

A hole 37 is formed in the first membrane 35 to expose a part of the sacrificial layer 33. The sacrificial layer 33 is etched to form a gap 38 (FIG. 3E). In this case, if the spring constant of the first membrane 35 is too small, the first membrane 35 may adhere onto the lower surface of the gap 38. Further, even after the sacrificial layer etching step is completed, the first membrane 35 may be greatly warped by a stress applied thereto and the performance may deteriorate. According to the present invention, the broadband is realized by changing the ratio of the electrode area to the gap area, and hence, even when the difference between the spring constants of the vibrating films 13 and 14 of FIG. 1B is reduced, the risk in the manufacture of the transducer can be reduced.

Figure 3F:
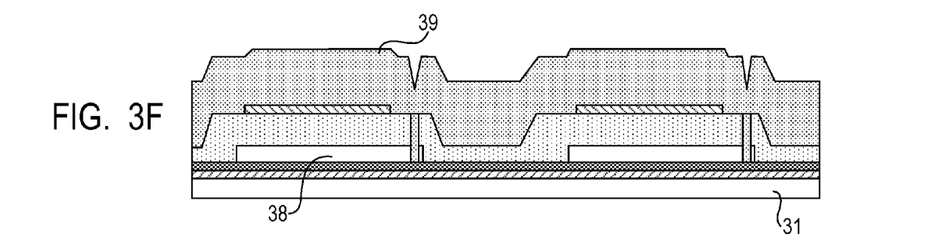

After that, the hole 37 is sealed, and simultaneously a second membrane 39 is formed (FIG. 3F). The first membrane, the second electrode 36, and the second membrane together constitute a vibrating film. This manufacturing method may be modified as follows. After the second electrode 36 is formed, the second membrane is formed, and a hole is formed in the second membrane and the first membrane. Then, the sacrificial layer is etched, and the hole is sealed. By manufacturing the capacitive transducer by the manufacturing method of the present invention, transmission/reception characteristics having a wide frequency band width can be realized. Further, by adjusting the ratio of the electrode area to the gap area, the pull-in voltages can be set to be closer to one another among cells having different frequency characteristics, and hence, even when a common voltage applying unit is used, the electromechanical transformer ratios of all the cells can be improved.

Now, the present invention is described in detail below by way of more specific examples.

Example 1

A capacitive transducer according to Example 1 of the present invention is now described. FIGS. 1A and 1B illustrate Example 1. The cell group 2 includes eight cells 4 and the cell group 3 includes eight cells 5, but the numbers of the cells are not limited thereto. However, if the number of cells in one of the cell groups is too large, the effect of increasing the band is reduced, and hence it is desired that the occupied areas of the cell groups 2 and 3 be as equal as possible.

As illustrated in FIG. 1A, when the vibrating films 13 and 14 or the gaps 9 and 10 in different kinds of cells are formed to be circular, the diameter thereof is 20 to 50 micrometers. The diameter of the gap 9 is larger than the diameter of the gap 10 in FIGS. 1A and 1B, but may be equal to each other. In this case, the area ratio of the second electrode 11 to the gap 9 is smaller than the area ratio of the second electrode 12 to the gap 10. Therefore, when the gap 9 and the gap 10 have equal areas, the second electrode 11 is smaller than the second electrode 12. The second electrodes 11 and 12 in FIG. 1A are illustrated by circles and connecting lines. However, the second electrodes 11 and 12 are not always required to be circular, but may be rectangular, polygonal, or the like.

The cell 4 in the cell group 2 is formed on a thermally oxidized monocrystalline silicon substrate 7 having a thickness of 300 micrometers. Although not illustrated, the thermal oxide film has a thickness of 100 nanometers to 2 micrometers. A first electrode 8 is formed on the substrate 7 by film formation and patterning. The cell 4 is constituted by forming the gap 9, a vibrating film 13 including the second electrode 11, and a support portion 15 on the first electrode 8. An insulating film 17 is formed between the gap 9 or the support portion 15 and the first electrode 8, to thereby insulate the first electrode 8 from the second electrode 11. This insulating film is a silicon oxide film formed by PECVD and having a thickness of 100 nanometers. The first electrode 8 is made of titanium having a thickness of 50 nanometers, and the second electrode 11 is made of aluminum having a thickness of 100 nanometers. The vibrating film 13 is a silicon nitride film except for the second electrode 11, and is formed by PECVD. The thickness of the vibrating film 13 below the second electrode 11 is 400 nanometers, and this portion serves also as an insulating film 18 for the first electrode 8. On the other hand, the silicon nitride film on the top of the second electrode 11 has a thickness of 1,000 nanometers. This silicon nitride film is formed with a tensile stress of 200 MPa or less.

In the above-mentioned structure, for example, the diameter of the gap 9 is 36 micrometers and the diameter of the second electrode 11 is 30 micrometers. The pull-in voltage is 150 V. The spring constant of the vibrating film 13 is 37 kN/m. As described above, the "spring constant" is calculated based on an average displacement of the electrode portion of the vibrating film caused by the electrostatic force. In Example 1, the area of the electrode portion corresponds to the area of the second electrode formed above the gap portion.

In the other cell 5, when the diameter of the gap 10 is 36 micrometers and the diameter of the second electrode 12 is 35 micrometers, the band is increased as compared to the case where the cells 4 and 5 have equal electrode areas. In this case, the vibrating film 14 has a spring constant of 64 kN/m, which is larger than the spring constant (37 kN/m) of the vibrating film 13 of the cell 4. In the case where the vibrating films of the cells 4 and 5 have different sizes, the effect of increasing the band can be enhanced by changing the ratio between the electrode area and the gap area. For example, in the cell 5, when the diameter of the gap 10 is 34 micrometers and the diameter of the second electrode 12 is 33 micrometers, the pull-in voltage is 174 V and the spring constant of the vibrating film 14 is 70 kN/m, thus increasing the frequency band width.

According to Example 1, among the cell groups, the vibrating films have different spring constants and the ratios of the electrode area to the gap area are varied, and hence the capacitive transducer having broadband characteristics can be realized.

Example 2

A capacitive transducer according to Example 2 of the present invention is now described. Example 2 is a modification of Example 1. FIG. 2 illustrates Example 2, illustrating the same cross-section as in FIG. 1B. The cell 4 in the cell group 2 has the same structure as in Example 1.

In a cell 105, a gap 110 has a diameter equal to that of the gap 9, and a second electrode 112 has a diameter equal to that of the second electrode 12 in Example 1. The structure of a vibrating film 114 is the same as that of the cell 4 in that the thickness below the second electrode 112 is 400 nanometers, but different in that the thickness of a silicon nitride film on the top of the second electrode is 1,100 nanometers. In this case, the vibrating film 114 has a spring constant of 77 kN/m, which is larger than the spring constant (37 kN/m) of the vibrating film 13. In this manner, the band is increased similarly to Example 1.

The thickness of the silicon nitride film above the second electrode 112 of the cell 105 is varied by the following method, for example. A metal film is formed on the cell group 2, and a silicon nitride film is formed thereon by PECVD. After that, only the region on the cell group 3 is protected by a photoresist, and the silicon nitride film is etched. In this case, when the metal film is made of an etching-resistant material, the cell group 2 is protected. After that, the photoresist is removed, and the metal film is removed, thereby manufacturing the structure of FIG. 2.

According to Example 2, among the cell groups, the vibrating films have different thicknesses and the ratios of the electrode area to the gap area are varied, and hence the capacitive transducer having broadband characteristics can be realized.

Example 3

A probe including the capacitive transducer described in the above-mentioned embodiment or examples is applicable to an object information acquisition apparatus using acoustic waves. An acoustic wave from an object is received by the capacitive transducer, and an output electric signal is used to acquire object information that reflects an optical property value of the object, such as a light absorption coefficient.

Figure 4:
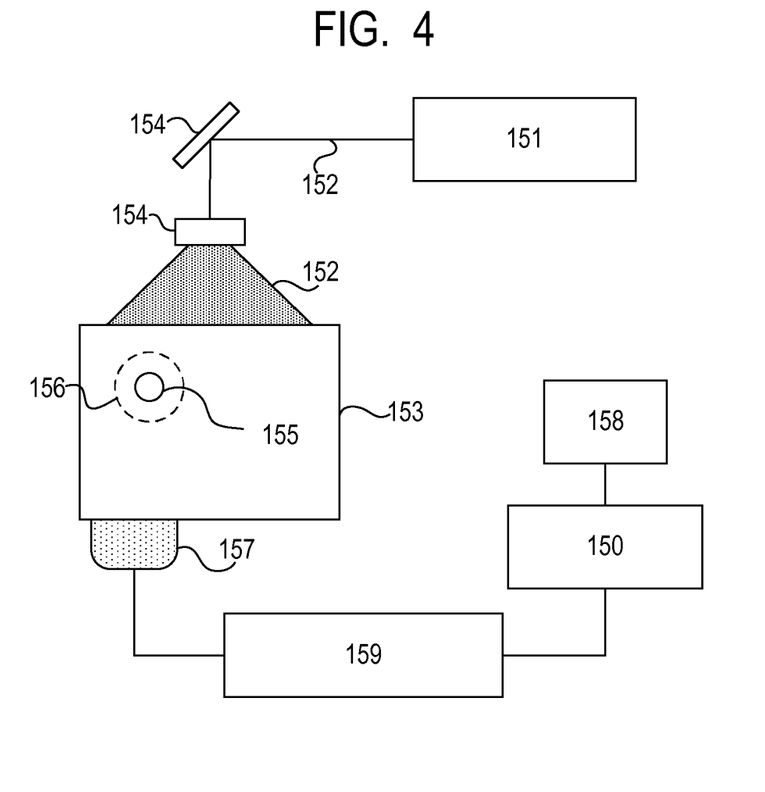
FIG. 4 is a diagram illustrating an exemplary apparatus for acquiring object information by using the capacitive transducer according to the present invention.

FIG. 4 illustrates an object information acquisition apparatus of Example 3 using a photoacoustic effect. Pulsed light 152 emitted from a light source 151 for generating light in the form of a pulse irradiates an object 153 via an optical member 154 such as a lens, a mirror, or an optical fiber. A light absorber 155 inside the object 153 absorbs energy of the pulsed light to generate a photoacoustic wave 156 as an acoustic wave. A probe 157, which is equipped with a casing that accommodates the capacitive transducer having broadband characteristics of the present invention, receives the photoacoustic wave 156 to convert the photoacoustic wave 156 into an electric signal, and outputs the electric signal to a signal processor 159. The signal processor 159 subjects the input electric signal to signal processing such as A/D conversion and amplification, and outputs the resultant signal to a data processor 150. The data processor 150 uses the input signal to acquire object information (object information that reflects an optical property value of the object, such as a light absorption coefficient) as image data. A display unit 158 displays an image based on the image data input from the data processor 150. The probe may be configured to scan mechanically or may be configured to be moved by a user, such as a doctor or an engineer, relative to the object (handheld type). It should be understood that the capacitive transducer as an electromechanical transducer of the present invention can be used also in an object diagnosis apparatus for detecting an acoustic wave from an object irradiated with the acoustic wave. Also in this case, the acoustic wave from the object is detected by the capacitive transducer, and a converted signal is processed by the signal processor, to thereby acquire information inside the object. In this case, the capacitive transducer of the present invention can be used to transmit an acoustic wave toward the object.

The capacitive transducer according to the present invention is applicable to an optical imaging device for acquiring information in a measurement target such as a living body, a conventional ultrasonic diagnosis apparatus, or the like. The capacitive transducer according to the present invention is applicable also to other applications including a supersonic flaw detector.

The capacitive transducer according to the present invention includes multiple kinds of cells that have different ratios between the electrode area and the gap area and are electrically connected in parallel. As a result, the capacitive transducer that includes multiple kinds of cells having different frequency characteristics of the electromechanical transformer ratios and therefore has a wide receiving frequency band width or transmitting frequency band width can be realized by flexible design in accordance with the requirements as they arise.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-151939, filed Jul. 6, 2012, which is hereby incorporated by reference herein in its entirety.

What is claimed is:

1. A capacitive transducer, comprising an element which has multiple types of cells, including cells of a first cell type and cells of a second cell type, each cell comprising:
   a first electrode; and
   a vibrating film comprising a second electrode, the second electrode being opposed to the first electrode with a gap therebetween, and
   the capacitive transducer having a common voltage applying unit for applying a voltage between the first electrode and the second electrode of cells of the first cell type and cells of the second cell type;
   wherein each type of cell has a different ratio of an area of the first electrode or the second electrode to an area of the gap when viewed from a normal direction of the vibrating film,
   wherein the first electrodes or the second electrodes in each type of cell are electrically connected together,
   wherein vibrating films of cells of the first cell type each have a larger spring constant than vibrating films of cells of the second cell type, and
   wherein the ratio of the area of the first electrode or the second electrode to the area of the gap in cells of the first cell type is larger than the ratio of the area of the first electrode or the second electrode to the area of the gap in cells of the second cell type;
   wherein the common voltage applying unit applies a common voltage to cells of the first cell type and cells of the second cell type, and the common voltage is smaller by 10% to 20% than a pull-in voltage of cells of the second cell type.

2. An object information acquisition apparatus, comprising:
   the capacitive transducer according to claim 1, configured to receive an acoustic wave and convert the acoustic wave into a signal; and
   a signal processor configured to process the signal output from the capacitive transducer to thereby acquire information on an object.

3. An object information acquisition apparatus according to claim 2, further comprising:
   a light source configured to emit light;
   wherein the capacitive transducer is configured to receive the acoustic wave, which is generated by an object that is irradiated by the light from the light source, and the signal processor is configured to process the signal, to thereby acquire information on the object.

4. A method of manufacturing the capacitive transducer according to claim 1, the method comprising for each cell:
   forming the first electrode;
   forming a sacrificial layer on the first electrode in order to form the gap;
   forming, on the sacrificial layer, at least a part of the vibrating film comprising the second electrode; and
   removing the sacrificial layer to form the gap,
   wherein the forming of the sacrificial layer and the forming of at least part of the vibrating film comprise setting different ratios of an area of the second electrode to an area of the sacrificial layer for each type of cell.

5. A capacitive transducer, according to claim 1, wherein for each cell the area of the first electrode and the second electrode is 50% or more of the area of the gap.

6. A capacitive transducer, according to claim 1, wherein the vibrating film of each cell further comprises an insulating membrane.

7. A capacitive transducer, according to claim 1, wherein cells of the first cell type have different frequency characteristics from cells of the second cell type.

8. A capacitive transducer, comprising an element which has multiple types of cells, including cells of a first cell type and cells of a second cell type, each cell comprising:
   a first electrode; and
   a vibrating film comprising a second electrode, the second electrode being opposed to the first electrode with a gap therebetween, and
   the capacitive transducer having a common voltage applying unit for applying a voltage between the first electrode and the second electrode of cells of the first cell type and cells of the second cell type;
   wherein each type of cell has a different ratio of an area of the first electrode or the second electrode to an area of the gap when viewed from a normal direction of the vibrating film,
   wherein the first electrodes or the second electrodes in each type of cell are electrically connected together,
   wherein vibrating films of cells of the first cell type each have a smaller area than vibrating films of cells of the second cell type, and
   wherein the ratio of the area of the first electrode or the second electrode to the area of the gap in cells of the first cell type is larger than the ratio of the area of the first electrode or the second electrode to the area of the gap in cells of the second cell type,
   wherein the common voltage applying unit applies a common voltage to cells of the first cell type and cells of the second cell type, and the common voltage is smaller by 10% to 20% than a pull-in voltage of cells of the second cell type.

9. A capacitive transducer, comprising an element which has multiple types of cells, including cells of a first cell type and cells of a second cell type, each cell comprising:

a first electrode; and a vibrating film comprising a second electrode, the second electrode being opposed to the first electrode with a gap therebetween, and the capacitive transducer having a common voltage applying unit for applying a voltage between the first electrode and the second electrode of cells of the first cell type and cells of the second cell type;

wherein each type of cell has a different ratio of an area of the first electrode or the second electrode to an area of the gap when viewed from a normal direction of the vibrating film, wherein the first electrodes or the second electrodes in each type of cell are electrically connected together, wherein vibrating films of cells of the first cell type each have a larger thickness than vibrating films of cells of the second cell type, and wherein the ratio of the area of the first electrode or the second electrode to the area of the gap in cells of the first cell type is larger than the ratio of the area of the first electrode or the second electrode to the area of the gap in cells of the second cell type, wherein the common voltage applying unit applies a common voltage to cells of the first cell type and cells of the second cell type, and the common voltage is smaller by 10% to 20% than a pull-in voltage of cells of the second cell type.

10. A capacitive transducer, comprising an element which has multiple types of cells, including cells of a first cell type and cells of a second cell type, each cell comprising:

a first electrode; and a vibrating film comprising a second electrode, the second electrode being opposed to the first electrode with a gap therebetween; and a common voltage applying unit for applying a voltage between the first electrode and the second electrode of cells of the first cell type and cells of the second cell type, wherein each type of cell has a different ratio of an area of the first electrode or the second electrode to an area of the gap when viewed from a normal direction of the vibrating film, wherein vibrating films of cells of the first cell type each have a larger spring constant than vibrating films of cells of the second cell type, wherein the ratio of the area of the first electrode or the second electrode to the area of the gap in cells of the first cell type is larger than the ratio of the area of the first electrode or the second electrode to the area of the gap in cells of the second cell type, and wherein the common voltage applying unit applies a common voltage to cells of the first cell type and cells of the second cell type, and the common voltage is smaller than a pull-in voltage $V_1$ that is smaller pull-in voltage of cells of the first cell type or the second cell type, and the common voltage is equal to or more than 80% of the pull-in voltage $V_1$.

11. The capacitive transducer, according to claim 10, wherein the first electrodes or the second electrodes in each type of cell are electrically connected together.

12. The capacitive transducer, according to claim 10, wherein each type of cell has a different ratio of the area of the second electrode to the area of the gap.

13. An object information acquisition apparatus, comprising:

the capacitive transducer according to claim 10, the capacitive transducer being further configured to receive an acoustic wave and convert the acoustic wave into a signal; and a signal processor configured to process the signal output from the capacitive transducer to thereby acquire information on an object.

14. A capacitive transducer, comprising an element which has multiple types of cells, including cells of a first cell type and cells of a second cell type, each cell comprising:

a first electrode; and a vibrating film comprising a second electrode, the second electrode being opposed to the first electrode with a gap therebetween; and a common voltage applying unit for applying a voltage between the first electrode and the second electrode of cells of the first cell type and cells of the second cell type, wherein each type of cell has a different ratio of an area of the first electrode or the second electrode to an area of the gap when viewed from a normal direction of the vibrating film, wherein vibrating films of cells of the first cell type each have a smaller area than vibrating films of cells of the second cell type, wherein the ratio of the area of the first electrode or the second electrode to the area of the gap in cells of the first cell type is larger than the ratio of the area of the first electrode or the second electrode to the area of the gap in cells of the second cell type, and wherein the common voltage applying unit applies a common voltage to cells of the first cell type and cells of the second cell type, and the common voltage is smaller than a pull-in voltage $V_1$ that is smaller pull-in voltage of cells of the first cell type or the second cell type, and the common voltage is equal to or more than 80% of the pull-in voltage $V_1$.

15. The capacitive transducer, according to claim 14, wherein the first electrodes or the second electrodes in each type of cell are electrically connected together.

16. The capacitive transducer, according to claim 14, wherein each type of cell has a different ratio of the area of the second electrode to the area of the gap.

17. An object information acquisition apparatus, comprising:

the capacitive transducer according to claim 14, the capacitive transducer being further configured to receive an acoustic wave and convert the acoustic wave into a signal; and a signal processor configured to process the signal output from the capacitive transducer to thereby acquire information on an object.

18. A capacitive transducer, comprising an element which has multiple types of cells, including cells of a first cell type and cells of a second cell type, each cell comprising:

a first electrode; and a vibrating film comprising a second electrode, the second electrode being opposed to the first electrode with a gap therebetween; and a common voltage applying unit for applying a voltage between the first electrode and the second electrode of cells of the first cell type and cells of the second cell type, wherein each type of cell has a different ratio of an area of the first electrode or the second electrode to an area of the gap when viewed from a normal direction of the vibrating film, wherein vibrating films of cells of the first cell type each have a larger thickness than vibrating films of cells of the second cell type, wherein the ratio of the area of the first electrode or the second electrode to the area of the gap in cells of the first cell type is larger than the ratio of the area of the first electrode or the second electrode to the area of the gap in cells of the second cell type, and wherein the common voltage applying unit applies a common voltage to cells of the first cell type and cells of the second cell type, and the common voltage is smaller than a pull-in voltage $V_1$ that is smaller pull-in voltage of cells of the first cell type or the second cell type, and the common voltage is equal to or more than 80% of the pull-in voltage $V_1$.

19. The capacitive transducer, according to claim 18, wherein the first electrodes or the second electrodes in each type of cell are electrically connected together.

20. The capacitive transducer, according to claim 18, wherein each type of cell has a different ratio of the area of the second electrode to the area of the gap.

21. An object information acquisition apparatus, comprising:
- the capacitive transducer according to claim 18, the capacitive transducer being further configured to receive an acoustic wave and convert the acoustic wave into a signal; and
- a signal processor configured to process the signal output from the capacitive transducer to thereby acquire information on an object.

* * * * *